United States Patent [19]

George

[11] 4,281,195
[45] Jul. 28, 1981

[54] PROCESS FOR THE PREPARATION OF SCHIFF'S BASES BY THE REACTION OF AROMATIC AMINES WITH KETONES

[75] Inventor: Joachim George, Leverkusen, Fed. Rep. of Germany

[73] Assignee: Bayer Aktiengesellschaft, Fed. Rep. of Germany

[21] Appl. No.: 110,806

[22] Filed: Jan. 10, 1980

[30] Foreign Application Priority Data

Jan. 18, 1979 [DE] Fed. Rep. of Germany ....... 2901863

[51] Int. Cl.³ ............................................ C07C 119/06
[52] U.S. Cl. .................................................. 564/271
[58] Field of Search ..................... 260/566 R; 564/271

[56] References Cited

U.S. PATENT DOCUMENTS 2,218,587  10/1940  Heinrich et al. ................. 260/566 R
2,533,723  12/1950  Dombrow ........................ 260/566 R Primary Examiner—Natalie Trousof
Assistant Examiner—L. Hendriksen
Attorney, Agent, or Firm—Connolly and Hutz

[57] ABSTRACT

Schiff's bases of the formula

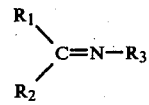

are obtained by reacting an amine $H_2N-R_3$ with a ketone

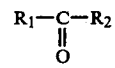

in presence of calcium hydrogen phosphate, apatite, aluminum oxide, aluminium hydroxide and/or Fuller's Earth and subsequent removing the water by azeotronic distillation.

The products are intermediates for the preparation of phenylene diamines which may be used as age resistors for rubber.

6 Claims, No Drawings

PROCESS FOR THE PREPARATION OF SCHIFF'S BASES BY THE REACTION OF AROMATIC AMINES WITH KETONES

This invention relates to a process for the preparation of Schiff's bases by the reaction of aromatic amines with ketones in the presence of catalysts.

The condensation of aromatic amines with ketones is an equilibrium reaction. It is shifted in favour of the formation of the Schiff's base by removal of the water of reaction. This may suitably be done by azeotropic distillation with a carrier agent.

If the reaction is carried out without additives which promote the formation of water of reaction, the required Schiff's base is only obtained in low yields after a comparatively long reaction time.

It has now been found that the formation of water of reaction and hence the preparation of the Schiff's base can be accelerated by the addition of certain compounds and at the same time the desired final product can be obtained in a high yield.

This invention therefore provides a process for the preparation of the Schiff's base corresponding to the formula (1):

by the reaction of a primary aromatic amine of the formula (2):

$$H_2N—R_3 \quad (2)$$

with a ketone of the formula (3):

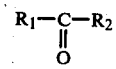

characterised in that the reaction is carried out in the presence of calcium hydrogen phosphate, apatite, aluminium oxide, aluminium hydroxide and/or Fuller's Earth and the water of reaction is removed by azeotropic distillation in known manner.

The reaction is illustrated by the following reaction scheme:

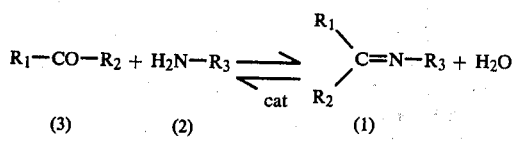

In the above formula (3), $R_1$ denotes a $C_1$–$C_3$ alkyl group such as methyl, ethyl, propyl or isopropyl preferably methyl, ethyl or isopropyl; $R_2$ denotes a straight chain or branched chain $C_2$–$C_9$ alkyl group such as ethyl, propyl, isopropyl, butyl, isobutyl, tertiary butyl, pentyl, isopentyl, hexyl, isohexyl, heptyl, isoheptyl, octyl, isooctyl, nonyl or isononyl, preferably ethyl, propyl, isopropyl, butyl, isobutyl or tertiary butyl; $R_1$ and $R_2$ may also be joined together to form a cyclic $C_5$–$C_7$ alkyl ring such as cyclohexyl or methyl cyclohexyl.

The following compounds are given as specific examples: butanone-(2); 3-methylbutanone-(2); 4-methylpentanone-(3); 5-methylhexanone-(2); 5-methylhexanone-(3); 4,4-dimethylpentanone-(2); cyclohexanone; and 4-methylcyclohexanone.

In the above formula (2), $R_3$ denotes an optionally substituted phenyl group such as phenyl, tolyl, xylyl, trimethylphenyl, ethylphenyl or diethylphenyl, any of which phenyl groups may be substituted with up to three $C_1$–$C_3$ alkyl groups, or it denotes a diphenylamine or triphenylamine group optionally substituted with one to three $C_1$–$C_3$ alkyl groups or amino groups, the substituents all being situated in that phenyl group which is not attached to the $NH_2$ group. This may be represented generally by the following formulae:

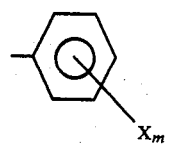

where
$X = C_1$–$C_3$ alkyl, and
$m = 0$ to 3, preferably 0 to 2
and

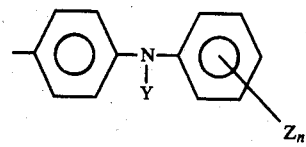

where
$Z = C_1$–$C_3$ alkyl or amino,
$Y = H$ or phenyl, and
$n = 0$ to 3, preferably 0 or 1.

The following compounds are given as specific examples:
aniline
o-, m- and p-toluidine,
m-phenylene diamine,
p-phenylene diamine,
4-ethyl aniline,
4-aminodiphenylamine,
2-methyl-4'-aminodiphenylamine,
3-methyl-4'-aminodiphenylamine,
4-methyl-4'-aminodiphenylamine, and
4,4'-diaminotriphenylamine.

In the end products of formula (1), the groups $R_1$, $R_2$ and $R_3$ have the meanings already indicated. The following Schiff's bases are examples:
N-1-methyl propylidene-phenylimine;
N-1,3-dimethyl butylidene-phenylimine;
N-1,4-dimethyl pentylidene-4-tolylimine;
N-cyclohexylidene-phenylimine; N-cyclohexylidene-4-tolylimine;
N,N'-bis(1,3-dimethyl butylidene)-1,4-diiminobenzene;
N,N'-bis(1,4-dimethyl pentylidene)-1,4-diiminobenzene;
N-1-methylpropylidene-4-iminodiphenylamine;
N-(1,3)-dimethyl butylidene-4-iminodiphenylamine;
N-1,4-dimethyl pentylidene-4-iminodiphenylamine;
N-cyclohexylidene-4-iminodiphenylamine;
N-1,3-dimethyl butylidene-4-imino-4'-methyl diphenylamine;

N-1,3-dimethyl butylidene-4-imino-3'-methyl diphenylamine;

N-1,3-dimethyl butylidene-4-imino-2'-methyl diphenylamine;

N-1,4-dimethyl pentylidene-4-imino-4-methyl diphenylamine;

N,N'-bis(1,3-dimethyl butylidene)-4,4'-diiminotriphenylamine.

The following are compounds which accelerate the formation of the Schiff's base according to the invention:

(1) Calcium hydrogen phosphate ($CaHPO_4$)

This product should be synthesized and anhydrous but not calcined.

(2) Apatite [$Ca_5(PO_4)_3(OH)$]

(3) Aluminium hydroxides and oxides

These products are preferably not annealed but only dried and should be soluble in warm dilute hydrochloric acid (5% at 70° C.).

(4) Fuller's Earths

Fuller's Earths are aluminium silicates of the montmorillonite type which have a large surface area and are activated by acid treatment. The products should be neutral in reaction (when made up into a slurry in water).

The following compounds are preferred: $CaHPO_4$, $Ca_5(PO_4)_3OH$, $AlOOH$, $Al_2O_3$ and $Al_2(SiO_2)_3$ (K, Na, Ca).

Compounds 1 to 4 used according to the invention accelerate the reaction, increase conversion and suppress side reactions such as the autocondensation of ketones. Compounds 1 to 4 may also be used as mixtures. They are generally put into the process in quantities of from 0.1 to 5% by weight, preferably 0.5 to 2% by weight, based on the amine.

The molar ratio of the amine (2) to the ketone (3) is generally in the range of from 1:1 to 1:10, preferably from 1:1 to 1:3.

The reaction temperature is generally from 50° to 150° C., preferably from 80° to 130° C.

The ketone itself is preferably used to function both as the carrier agent and as the solvent. Hydrocarbons such as n- and isohexanes, n- and isoheptanes, and n- and isooctanes, cyclohexane, methyl cyclohexanes, benzene, toluene or xylenes and chlorinated hydrocarbons such as dichloromethane, dichloroethane, trichloromethane (chloroform) and trichloroethylene may be used as auxiliary carriers or solvents. Alkanols such as 4-methylpentanol-2 and cyclohexanol may also be used as auxiliary solvents. The ratio by weight of the ketone to the auxiliary solvents or carriers is preferably in the range of from 1:0.2 to 1:5.

The Schiff's bases obtained by the process according to the invention are valuable intermediate products for the preparation of substituted phenylene diamine which may be used, for example, as an age resistor for rubbers.

The invention is illustrated by the following Examples:

Example 1
(2,4-dimethyl-butylene-4-iminodiphenylamine)

1 mol of 4-aminodiphenylamine and 2.5 mol of methylisobutyl ketone are boiled under reflux over a water separator in the presence of 5 g of calcium hydrogen phosphate. The sump temperature settles at 130° C. 17 g of water have been split off after 3 hours. The conversion is 92%.

When the reaction is carried out without a catalyst under the same conditions, only 62% conversion is obtained after 6 hours. No further increase in conversion can be achieved by prolonging the reaction.

Example 2
(2,5-dimethyl-pentylene-4-iminodiphenylamine)

Methyl isoamyl ketone is used instead of methyl isobutyl ketone in a reaction carried out under the same conditions as in Example 1. The sump temperature is established at 120° C. The conversion is 85%.

I claim:

1. A process for preparing a Schiff's base of the formula $$\begin{array}{c} R_1 \\ \phantom{R}\diagdown \\ \phantom{xx}C=N-R_3 \\ \phantom{R}\diagup \\ R_2 \end{array}$$

wherein $R_1$ when taken separately is alkyl having 1 to 3 carbon atoms, $R_2$ when taken separately is alkyl having 2 to 9 carbon atoms, $R_1$ and $R_2$ when taken together with the carbon atom to which they are attached form a saturated hydrocarbon ring having from 5 to 7 carbon atoms and $R_3$ is

[structure: phenyl with $X_m$ substituents] or [structure: diphenylamine with N–Y linkage, $X_m$ and $Z_n$ substituents]

wherein
X is alkyl having 1 to 3 carbon atoms,
m is 1 to 3,
Y is hydrogen or phenyl,
Z is alkyl having 1–3 carbon atoms or amino and
n is 1 to 3, said process comprising reacting an amine of the formula $H_2N-R_3$ wherein $R_3$ is aforesaid with a ketone of the formula $$R_1-\underset{\underset{O}{\|}}{C}-R_2$$

wherein $R_1$ and $R_2$ are as aforesaid in a molar ratio of amine to ketone of from 1:1 to 1:10 and in the presence of a catalytic amount of at least one catalyst selected from the group consisting of calcium hydrogen phosphate, apatite, aluminum oxide and aluminum hydroxide and removing water of reaction by azeotropic distillation.

2. The process of claim 1 wherein the amine ratio of the amine to the ketone is from 1:1 to 1:3.

3. The process of claim 1 wherein the catalyst is used in a quantity of from 0.1 to 5% by weight, based on the weight of amine.

4. The process of claim 1 wherein the catalyst is used in a quantity of from 0.5 to 2% by weight, based on the weight of amine.

5. The process of claim 1 wherein said reaction is carried out at from 50° to 150° C.

6. The process of claim 1 wherein said reaction is carried out at from 80° to 130° C.

* * * * *